United States Patent [19]

Faden

[11] Patent Number: 5,686,420

[45] Date of Patent: Nov. 11, 1997

[54] THYROTROPIN-RELEASING HORMONE ANALOGS AND METHOD OF USE

[75] Inventor: Alan I. Faden, Mill Valley, Calif.

[73] Assignee: Georgetown University, Washington, D.C.

[21] Appl. No.: 379,797

[22] Filed: Jan. 27, 1995

Related U.S. Application Data

[63] Continuation of Ser. No. 988,344, Dec. 9, 1992, abandoned, which is a continuation of Ser. No. 435,567, Nov. 13, 1989, abandoned, which is a continuation-in-part of Ser. No. 387,416, Jul. 31, 1989, abandoned, which is a continuation of Ser. No. 253,879, Oct. 5, 1988, abandoned, which is a continuation of Ser. No. 58,339, Jun. 5, 1987, abandoned, and Ser. No. 400,189, Aug. 28, 1989, abandoned, which is a continuation of Ser. No. 253,880, Oct. 5, 1988, abandoned, which is a continuation of Ser. No. 58,380, Jun. 5, 1987, abandoned.

[51] Int. Cl.$^6$ .............................. A61K 38/00; C07K 5/00; C07K 7/00; C07K 17/00

[52] U.S. Cl. .............................................. 514/18; 530/331

[58] Field of Search .............................. 514/18; 530/331

[56] References Cited

U.S. PATENT DOCUMENTS

| | | |
|---|---|---|
| 3,959,248 | 5/1976 | Veber et al. . |
| 4,100,152 | 7/1978 | Fujmo et al. . |
| 4,426,378 | 1/1984 | Holaday . |
| 4,564,609 | 1/1986 | Tamura et al. . |
| 4,608,365 | 8/1986 | Engel . |
| 4,610,821 | 9/1986 | Tamura et al. . |
| 4,636,567 | 1/1987 | Tamura et al. . |
| 4,711,878 | 12/1987 | Sugano et al. . |
| 4,719,207 | 1/1988 | Tamura et al. . |
| 4,906,614 | 3/1990 | Giertz et al. . |

FOREIGN PATENT DOCUMENTS

| | | |
|---|---|---|
| 0123444 | 10/1984 | European Pat. Off. . |
| 123444 | 10/1984 | European Pat. Off. . |
| 60-172996 | 6/1985 | Japan . |

OTHER PUBLICATIONS

Yale J. Med. and Pharm Chem. vol. 1 p. 121 (1959) CA 106:19024q.

Fukuda et al Chem. Pharm. Bull. p. 1667 (1980).

Flohe et al Thyrotropin–Releasing Hormone, ed. Griffiths and Bennet pp. 327–340 (1983).

Faden et al Neurology vol. 35 p. 1331 (1985).

Griffiths Psychoneuroendocin. vol. 10 p. 225 (1985).

Cecil Textbook of Medicine p. 2077 (1992).

Kirk et al ACS Symposium Series No. 28 pp. 32–36 1976.

Feuerstein et al Neuropeptides vol. 4 pp. 303–310 1984.

Flohé, L., et al., "Biological Effects of Degradation–Stabilized TRH Analogues, *Thyrotropin–Releasing Hormone*", Editors: Griffiths, E.C., and Bennett, G.W., Raven Press, New York, pp. 327–340 (1983).

Feuerstein, G., et al., "Differential Effect of Fluorinated Analogs of TRH on the Cardiovascular System and Prolactin Release", *Neuropeptides*, vol. 4, pp. 303–310 (1984).

Faden, A.I., et al., "Effect of TRH analogs on neurologic recovery after experimental spinal trauma", *Neurology*, vol. 35, pp. 1331–1334 (1985).

Fukuda, N., et al., "Synthesis and Pharmacology of TRH Analogs to Separate Central Nervous Action from Endocrine Activity", *Chem. Pharm. Bull.*, vol. 28, pp. 1667–1672 (1980).

Labrie, F., et al., "Binding of Thyrotropin–Releasing Hormone to Plasma Membranes of Bovine Anterior Pituitary Gland", *Proc. Natl. Acad. Sci. USA*, vol. 69, pp. 283–287 (1972).

Griffiths, E.C., "Thyrotropin Releasing Hormone: Endocrine and Central Effects", *Psychoneuroendocrin*, vol. 10, pp. 225–235 (1985).

Labroo, et al., "Synthesis and Cardiovascular Activity of Imidazole Substituted Analogs of TRH", CA:106:19024q, (1987).

Feuerstein, et al., "Differential effect of fluorinated analogs of TRH on cardiovascular system & prolactin release", CA:101:164032s (1984).

Vonhofet, et al., "Receptor binding of fluorinated histidine analog of TRA", CA:111:50695m (1989).

Labroo et al., "Sysnthesis and Biological Activity of Fluoroimidazole TRH", *Biochem & Biophys. Res. Comm.*, vol. 113, No. 2 (1983).

Panton, et al. "In vivo and In vitro studies of effects of halogenated histidine analogs on plasmodium falergam", *Ant. Angrib. & Chemotherapy*, vol. 11, pp. 1655–1659 (1988).

Denklewalter, et al., "Progress in Drug Research Pharmaceutiques", vol. 10, pp. 510–512 (1966).

Kirk, K.L., et al., "Biochemistry and Pharmacology of Ring–Fluorinated Imadazoles," *Biochemistry Involving Carbon–Fluorine*, ACS Symposium Series, No. 28, pp. 23–36 (1976).

Friderich, E., et al., "Activity of Thyroliberin Analogs with a Modified Pyroglutamyl Residue on the Central Nervous System", *Structure and Activity of Natural Peptides*, Editors: Voelter, W., and Weitzel, G., Walter de Gruyter, Berlin, pp. 461–481 (1981).

*Primary Examiner*—Toni R. Scheiner
*Assistant Examiner*—Sheela J. Huff
*Attorney, Agent, or Firm*—Oliff & Berridge

[57] ABSTRACT

A series of novel thyrotropin-releasing hormone analogs wherein the C-terminal prolineamide moiety has been preserved, the N-terminal moiety comprises one of five different ring structures and the histidyl moiety is substituted with $CF_3$, $NO_2$ or a halogen. A method of use of the analog for the treatment of neurologic disorders is also provided.

24 Claims, No Drawings

THYROTROPIN-RELEASING HORMONE ANALOGS AND METHOD OF USE

CROSS-REFERENCE TO RELATED APPLICATIONS

This is a continuation of application Ser. No. 07/988,344, filed Dec. 9, 1992, now abandoned, which is a continuation of application Ser. No. 07/435,567, filed Nov. 13, 1989, now abandoned, which is a continuation-in-part of application Ser. No. 07/387,416, filed Jul. 31, 1989, now abandoned, which is a continuation of application Ser. No. 07/253,879, filed Oct. 5, 1988, now abandoned, which is a continuation of application Ser. No. 07/058,339, filed Jun. 5, 1987, now abandoned, and a continuation of application Ser. No. 07/400,189, filed Aug. 28, 1989, now abandoned, which is a continuation of application Ser. No. 07/253,880, filed Oct. 5, 1988, now abandoned, which is a continuation of application Ser. No. 07/058,380, filed June 5, 1987, now abandoned.

TECHNICAL FIELD

The present invention relates to a series of compounds and their use in the treatment of neurologic disorders, and more particularly relates to a series of novel thyrotropin-releasing hormone analogs for use in the treatment of brain and spinal cord trauma.

BACKGROUND OF THE INVENTION

Neurologic disorders are defined herein as any abnormal central nervous system conditions including, but not limited to, brain and spinal cord trauma; stroke; neurodegenerative disorders such as amyotropic lateral sclerosis or spinocerebellar degeneration; and coma or stupor due to anesthetics or an overdose of a drug.

Central nervous system trauma, caused by injuries such as spinal injuries and head injuries, are becoming increasingly prevalent. Many of these injuries are caused by automobile accidents. Other circumstances causing spinal or head injuries include serious falls, diving accidents, crushing industrial injuries, and gunshot or stab wounds.

Traumatic brain or spinal injuries cause tissue damage through both direct, or mechanical injury to the tissue, and indirect or secondary means. Secondary tissue damage is believed to be caused by the activation of endogenous, autodestructive, neurochemical substances.

Thyrotropin-releasing hormone (TRH), which has been identified as L-pyroglutamyl-L-histidyl-L-prolineamide, is a small peptide that has been found in various cells of the body, mainly the neural cells of the central nervous system. The structure of TRH is shown below:

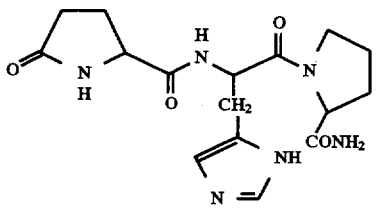

The right portion of the molecule is known to those skilled in the art as the "prolineamide", "NH₂" or "C-terminal" portion; the center portion of the molecule is known as the "histidyl" portion; and the left portion of the molecule is known as the "pyroglutamyl", "COOH-terminal" or "N-terminal" portion.

Endogenous TRH can act as either a neurotransmitter or a neuromodulator or both. A major percentage of this hormone is released from the hypothalamic nerve terminals in the median eminence to stimulate the secretion of thyroid stimulating hormone, the function for which TRH is named. TRH is also found in other areas of the central nervous system, and in tissues of the body such as the alimentary tract, pancreas, placenta and retina of the eye.

The function of TRH in these various areas of the body is largely unknown. However, numerous behavioral studies have shown that the peripheral or central administration of TRH induces arousal and counteracts the depressant effects of many drugs including neuroleptics, alcohol and anaesthetics.

TRH has recently been shown to antagonize many of the effects of the endogenous opiates including spinal cord injury. (Faden et al., Thyrotropin-releasing hormone improves neurologic recovery after spinal trauma in cats, *N. Engl. J. Med.*, 305:1063–1067 (1981)). The advantage of TRH is that it acts as a physiological opiate antagonist without affecting nociception.

The major disadvantage of the use of TRH in central nervous system injury is that the hormone is very rapidly metabolized. Therefore, high doses or continuous infusions are necessary for effective treatment. The short plasma half-life (4–5 min) is most likely due to rapid degradation of the peptide at both the COOH— and $NH_2$ terminals of the molecule. Cleavage of the pyroglutamyl moiety of TRH by peptidases causes formation of the metabolite cyclo-histidyl-proline-diketopiperazine. Deamidation of TRH results in the formation of the free acid TRH-OH.

A number of peptidase-resistant analogs of TRH have been synthesized, mainly for research purposes. They were developed initially as antidepressants. Most of these analogs have been found to have centrally active effects such as endocrine, analeptic and autonomic effects.

What is needed is a compound that is effective in treating neurologic disorders, especially a compound that is effective in reducing secondary brain and spinal injury in patients suffering from traumatic central nervous system injury, without affecting nociception, and without being rapidly metabolized.

SUMMARY OF THE INVENTION

The present invention comprises a series of compounds and their use in the treatment of neurologic disorders. The series of compounds comprise novel thyrotropin-releasing hormone analogs. The neurologic disorder is treated by administering an effective amount of a compound to a patient.

In the preferred embodiments of the present invention, the compound comprises a TRH analog wherein the C-terminal prolineamide moiety has been preserved and the two remaining peptide components have been modified. The N-terminal portion of the analog comprises one of five different ring structures. The histidyl portion of the analog is modified by substitutions at the two and four carbon positions. The resulting preferred embodiments of the novel analog are shown below:

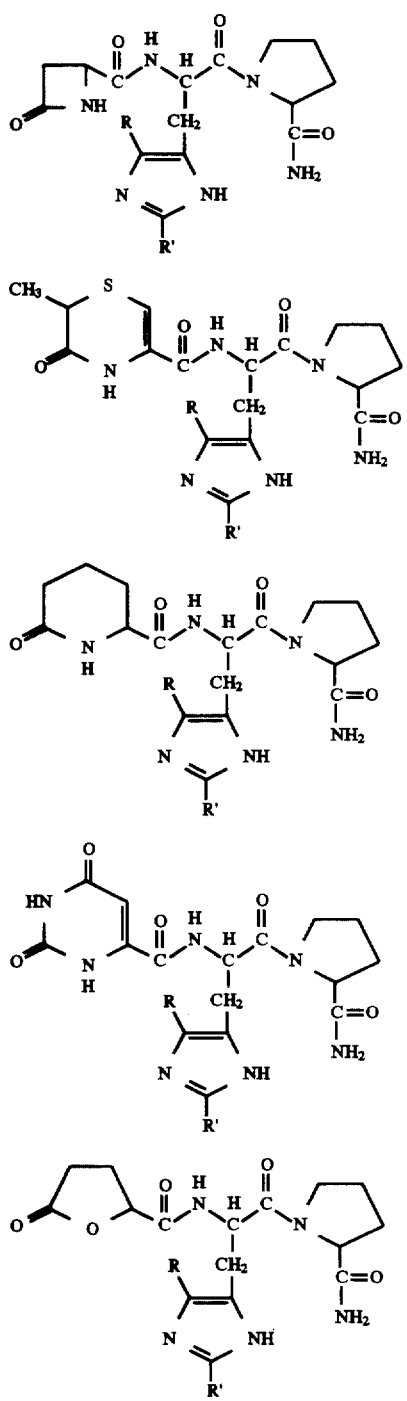

The histidyl portion of each compound is modified so that R=CF$_3$, NO$_2$, F, I or Br and R'=H; or R=H and R'=CF$_3$; or R and R'=I or Br.

Accordingly, it is an object of the present invention to provide a novel TRH analog.

It is a further object of the present invention to provide a novel TRH analog that is effective in the treatment of central nervous system injury.

It is a further object of the present invention to provide a novel TRH analog that is not readily metabolized.

It is a further object of the present invention to provide a novel TRH analog having enhanced central nervous system penetration.

It is a further object of the present invention to provide an effective treatment for neurologic disorders.

It is a further object of the present invention to provide an effective treatment for brain and spinal cord trauma.

It is a further object of the present invention to provide an effective treatment for the secondary effects of central nervous system injury.

It is a further object of the present invention to provide an effective treatment for hypovolemic or anaphylactic shock.

It is a further object of the present invention to provide a compound that will increase the acceptance of a tissue transplant.

These and other objects, features and advantages of the present invention will become apparent after a review of the following detailed description of the disclosed embodiment and the appended claims.

DETAILED DESCRIPTION OF THE INVENTION

The present invention comprises a series of compounds and their use in the treatment of neurologic disorders. The compounds are novel thyrotropin-releasing hormone analogs which are preferably used in the treatment of brain and spinal cord trauma. The injury is treated by administering an effective amount of a compound to the patient wherein the compound preferably reduces the secondary effects of the trauma by optimally antagonizing the actions of autodestructive biochemical substances, such as endogenous opioids, without being rapidly metabolized. Preferably, the compound penetrates the central nervous system.

In a first preferred embodiment of the present invention, the compound is a TRH analog having the following structure:

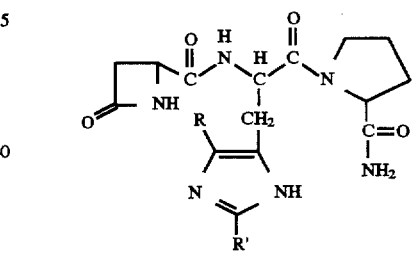

wherein R or R' or both are halogens such as R=I and R'=I or R=F and R'=H, or R=I and R'=H, or R=Br and R'=Br, or R=Br and R'=H.

Alternatively, R=CF$_3$ and R'=H or the R and R' are reversed so that R=H and R'=CF$_3$. In another alternative, R=NO$_2$ and R'=H.

In a second preferred embodiment of the present invention, the compound is a TRH analog having the following structure:

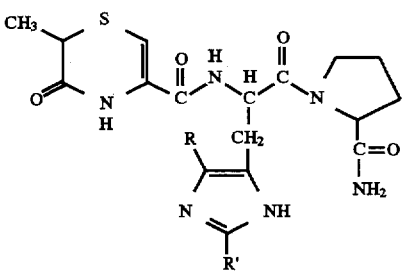

wherein R=NO$_2$ and R'=H.

Alternatively, R=CF₃ and R'=H or the R and R' are reversed so that R=H and R'=CF₃. In another alternative, R or R' or both are halogens such as R=F and R'=H, or R=I and R'=I, or R=I and R'=H, or R=Br and R'=Br, or R=Br and R'=H.

In a third preferred embodiment of the present invention, the compound is a TRH analog having the following structure:

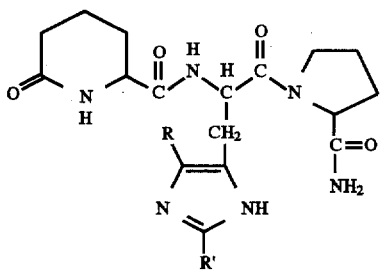

wherein R=CF₃ and R'=H.

Alternatively, the R and R' are reversed so that R=H and R'=CF₃. In another alternative, R=NO₂ and R'=H. In yet another alternative, R or R' or both are halogens such as R=F and R'=H, or R=I and R'=I, or R=I and R'=H, or R=Br and R'=Br, or R=Br and R'=H.

In a fourth preferred embodiment of the present invention, the compound is a TRH analog having the following structure:

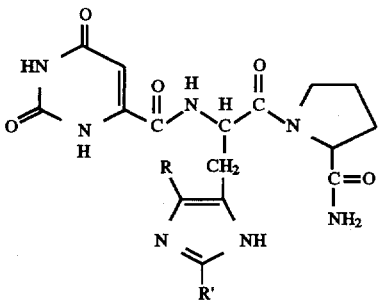

wherein R=CF₃ and R'=H.

Alternatively, the R and R' are reversed so that R=H and R'=CF₃. In another alternative, R=NO₂ and R'=H. In yet another alternative, R or R' or both are halogens such as R=F and R'=H, or R=I and R'=I, or R=I and R'=H, or R=Br and R'=Br, or R=Br and R'=H.

In a fifth preferred embodiment of the present invention, the compound is a TRH analog having the following structure:

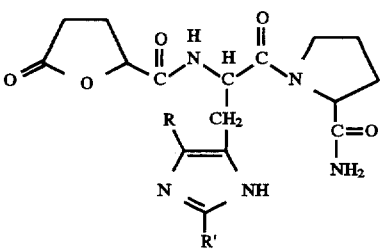

wherein R=CF₃ and R'=H.

Alteratively, the R and R' are reversed so that R=H and R'=CF₃. In another alternative, R=NO₂ and R'=H. In yet another alternative, R or R' or both are halogens such as R=F and R'=H, or R=I and R'=I, or R=I and R'=H, or R=Br and R'=Br, or R=Br and R'=H.

The first preferred novel TRH analog of the present invention is synthesized by starting with the compound N-[[(5)-4-oxo-2-azetidinyl]carbonyl]-L-histadyl-L-prolineamide dihydrate known in the industry as YM-14673, which is available through Yamanouchi Pharmaceutical Co. LTD (Tokyo, Japan). The various substitutions are created in accordance with the method of Labroo, V. M., Feurerstein, G., and Cohen, L. A., in "Peptides: Structure and Function" Proceedings of the Ninth American Peptide Symposium, Deber, Hruby and Kopple, eds., pp. 703–706, 1985, which is incorporated herein by reference. The second preferred novel TRH analog is synthesized by starting with the compound orotyl-L-histidyl-L-prolineamide, known in the industry as CG 3703, which is available through Chemie Grunenethal (Stolberg, West Germany). The various substitutions are created in accordance with the method of Labroo cited above. The third preferred novel TRH analog of the present invention is synthesized by starting with the thryotropin releasing hormone and modifying it in accordance with method known to those skilled in the art. The various substitutions are created in accordance with the method of Labroo cited above. The fourth preferred novel TRH analog of the present invention is synthesized by starting with the compound known in the industry as CG 3509, which is available through Chemie Grunenethal (Stolberg, West Germany). The various substitutions are created in accordance with the method of Labroo cited above. The fifth preferred novel TRH analog of the present invention is synthesized by starting with the compound γ-butyrolactone-γ-carbonyl-L-histidyl-L-proline amide citrate, known in the industry as DN 1417, which is available through Takeda Chemical Industries, Ltd. (Osaka, Japan). The various substitutions are created in accordance with the method of Labroo cited above.

An effective dose of the TRH analog of the present invention comprises an amount of the analog sufficient to reduce secondary injury by blocking or reducing the release of injurious endogenous substances. Preferably, the effective dose is from approximately 0.1 to 10.0 mg/kg body weight of the patient. This dose is preferably administered every 4–6 hours for approximately 24 hours to treat trauma. It will be understood by those skilled in the art that the compound is administered chronically for the treatment of other neurologic disorders such as stroke; systic, hypovolemic or anaphylactic shock; neurodegenerative disorders such as amyotropic lateral sclerosis or spinocerebellar degeneration; and unconsciousness or subconsciousness due to anesthetics or overdoses.

Most preferably the effective dose of the TRH analog of the present invention is approximately 1.0 mg/kg body weight of the patient administered every 4–6 hours within the first 24 hours after trauma.

Although not wanting to be bound by the following hypothesis, it is believed that the preferred embodiments of the TRH analog of the present invention increase neurologic recovery by blocking the actions of several injury factors including opioids, leukotrienes, and platelet activating factor released as a consequence of the trauma. The analog may also inhibit lipid membrane breakdown, i.e. reduce the release of polyunsaturated fatty acids and eicosanoids which are toxic to central nervous system tissue. The TRH analog may also act by maintaining magnesium homeostasis. Furthermore, halogenation of the histidyl portion of the analog may enhance blood-brain barrier penetration.

The therapeutic route of administration of the compound of the present invention includes, but is not limited to, intravenous, intramuscular, subcutaneous, and oral administration. Preferably, the compound is administered intravenously.

The compound of the present invention can be administered as a liquid or gel by any of the above described routes of administration or orally in the form of a solid tablet. Preferably, the compound is administered to the patient in the form of a liquid solution, the solution comprising an effective amount of active ingredient compound and a pharmaceutically acceptable solution.

The pharmaceutically acceptable solution includes any solution that is safe for injection or ingestion and is biologically inert so that it does not interfere with the active ingredient. The preferred pharmaceutically acceptable solution comprises an isotonic solution suitable for injection into a patient. For example, the isotonic solution may contain water, salt, and conventional ingredients such as glucose. The pharmaceutically acceptable solution may also contain purified water mixed with preservatives, flavors, colorants, flavor enhancing agents, and other additives such as sodium benzoate, methyl paraben, propylene glycol, glycerin, sorbitol, alcohol, sucrose, saccharin, menthol and citric acid.

As described above, the TRH analog of the present invention is preferably used to treat brain and spinal cord injuries caused by central nervous system trauma. However, the TRH analog of the present invention can also be administered to a patient undergoing a tissue transplant by reducing secondary traumatic injury associated with the transplant process.

The following specific examples will illustrate the invention as it applies in particular to improving neurologic function. It will be appreciated that other examples will be apparent to those of ordinary skill in the art and that the invention is not limited to these specific illustrative examples.

EXAMPLE 1

An experiment is described to illustrate the effect of the following TRH analog on neurological function:

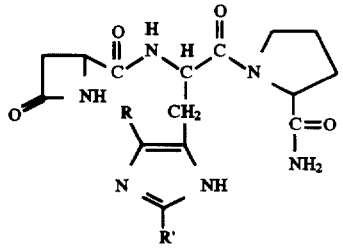

wherein R and R'=I.

Models

Traumatic Brain Injury

Following anesthesia with pentobarbital (60 mg/kg, i.p.) male, Sprague-Dawley rats (400±25 g) are subjected to traumatic brain injury utilizing a lateral, fluid-percussion.

The fluid-percussion device used to produce experimental brain injury is a Plexiglas cylindrical reservoir, 60 cm long and 4.5 cm in diameter, bounded at one end by a Plexiglas, cork-covered piston mounted on O rings. The opposite end of the reservoir is fitted with a 2-cm-long metal housing on which a transducer (Gould) is mounted and connected to a 5-mm tube (2 mm ID) that terminates with a male Luer Lok fitting. At the time of injury, the tube is connected to a female Luer Lok fitting that has been chronically implanted over the exposed cortex of the rat. After the entire system is filled with 37° C. isotonic saline, injury is induced by a metal pendulum, which strikes the piston of the device from a predetermined height. The device produces a pulse of increased intracranial pressure of fairly constant duration (21–23 ms) by injecting varying volumes of saline into the closed cranial cavity. Brief displacement and deformation of neural tissue results from the rapid epidural injection of saline, and increased magnitude of tissue deformation is associated with an increased magnitude of brain injury. The magnitude of injury is regulated by varying the height of the pendulum, which results in corresponding variations in intracranial pressure pulses expressed in atmospheres. These pressure pulses are measured extracranially by a transducer (housed in the injury device) at the time of injury, recorded on a storage oscilloscope, and photographed with a Polaroid camera.

Spinal Cord Injury

Male, Sprague-Dawley rats (300±25 g are anesthetized with sodium pentobarbital (60 mg/kg, i.p.) and laminectomy is performed at $T_9$. The spinal cord is injured using a modification of the weight-drop method in which a 10 g weight is dropped a distance of 5 cm through a guide tube onto a Teflon impounder plate that strikes the exposed spinal cord. This 50 g-cm impact force causes severe, reproducible, but incomplete tissue injury (control animals show moderately severe spastic paraparesis 4 weeks after trauma). A catheter is inserted into the jugular vein for drug administration.

Drug Treatment

Traumatic Brain Injury

At 30 min following a 2.5 atmosphere level injury, animals are randomly assigned to one of two treatment groups (each n=8): the above-described TRH analog (1.0 mg/kg) or equal volume (1 cc) physiological saline, each administered as a slow intravenous bolus injection over 60 sec.

Traumatic Spinal Cord Injury

At 15 min following spinal cord trauma, animals are randomly assigned to one of two treatment groups: the above-described TRH analog (n=17) or equal volume (1 cc) physiological saline (n=15), each administered as a slow intravenous bolus injection over 60 sec.

Neurological Evaluation

Traumatic Brain Injury

Neurological function is evaluated daily over a 2-week period by an individual unaware of treatment group. Animals are evaluated separately for five tests of motor function, each scored on an ordinal scale from 0 (severely impaired) to 4 (normal function). Tests include: (a) ability to maintain position on an inclined plane in either the vertical or horizontal position for 5 sec; (b) forelimb flexion following suspension by the tail; (c) the degree of resistance to lateral pulsion; and (d) activity monitored in a computerized Opto-Varimex activity chamber (Columbus Instruments). Each of the five individual scores—vertical angle, horizontal angle, forelimb flexion, lateral pulsion, and activity—are added to yield a composite neurological score that ranges from 0 to 20. Animals are maintained for 2 weeks.

Spinal Cord Injury

Animals are scored blindly over a 4-week period after trauma utilizing an 8-point ordinal scale based on motor function: 0=no spontaneous movements; 1=spontaneous movements but unable to support weight; 2=supports weight only briefly; 3=stands, but unable to walk; 4=walks, but with severe spasticity and ataxia; 5=walks, but with moderate marked spasticity; 6=walks with minimal spasticity; 7=normal motor function. Animals are also graded as either walkers (score=4–7) or nonwalkers (score=0–3). In addition, rats are scored on their ability to maintain themselves on an inclined plane in the vertical and horizontal positions for 5 sec, with the maximal angle noted.

Results

Composite neurological scores at 2 weeks after traumatic brain injury are significantly higher in the treatment group animals than in controls. TRH analog treatment also improves neurological outcome at 4 weeks after traumatic spinal cord injury.

The present study shows that the above-described TRH analog, administered as a single bolus intravenous injection after trauma, significantly improves neurological outcome following fluid-percussion-induced lateral brain injury and impact spinal cord trauma in rats.

It should be understood, of course, that the foregoing relates only to preferred embodiments of the present invention and that numerous modifications or alterations may be made therein without departing from the spirit and the scope of the invention as set forth in the appended claims.

I claim:

1. A compound having the following formula:

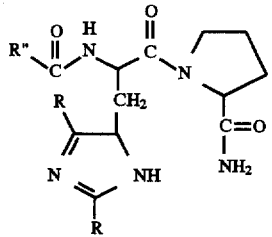

wherein R" is selected from the group consisting of:

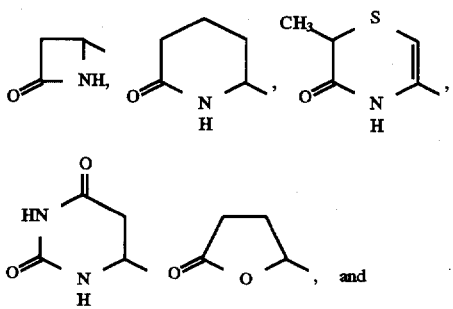

R and R' are both I.

2. The compound of claim 1, wherein R" is

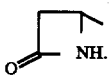

3. A compound having the following formula:

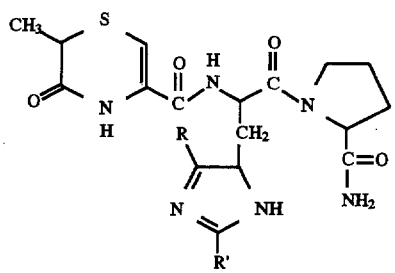

wherein R and R' are respectively:

(a) halogen and halogen;
(b) halogen and hydrogen;
(c) $CF_3$ and hydrogen;
(d) hydrogen and $CF_3$; or
(e) $NO_2$ and hydrogen.

4. The compound of claim 1, wherein R" is

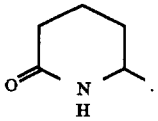

5. The compound of claim 1, wherein R" is

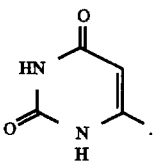

6. The compound of claim 1, wherein R" is

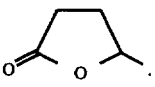

7. A method for the treatment of effects of neurologic damage in an animal, comprising administering to an animal suffering from neurologic damage a neurologic damage effect treating effective amount of a compound having the following formula:

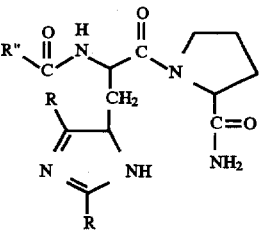

wherein R" is selected from the group consisting of:

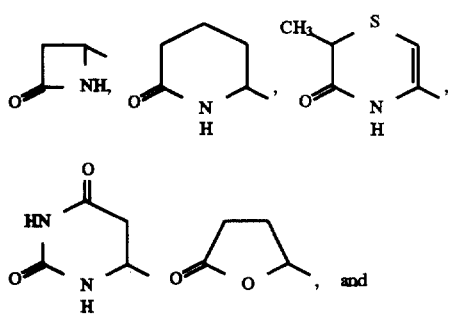

wherein R and R' are respectively:

(a) halogen and halogen;
(b) halogen and hydrogen;
(c) CF$_3$ and hydrogen;
(d) hydrogen and CF$_3$; or
(e) NO$_2$ and hydrogen, wherein said neurologic damage is brain trauma.

8. A method for the treatment of effects of neurologic damage in an animal, comprising administering to an animal suffering from neurologic damage a neurologic damage effect treating effective amount of a compound having the following formula:

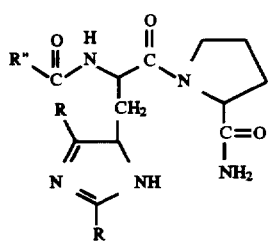

wherein R" is selected from the group consisting of:

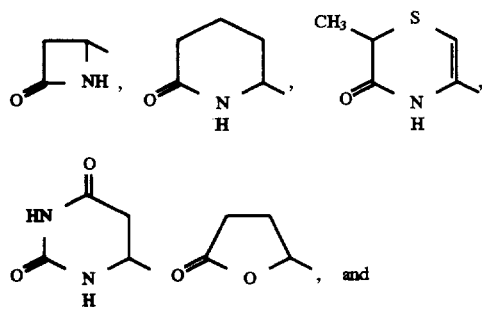

wherein R and R' are respectively:

(a) halogen and halogen;
(b) halogen and hydrogen;
(c) CF$_3$ and hydrogen;
(d) hydrogen and CF$_3$; or
(e) NO$_2$ and hydrogen, wherein said neurologic damage is caused by a stroke.

9. A method for the treatment of effects of neurologic damage in an animal, comprising administering to an animal suffering from neurologic damage a neurologic damage effect treating effective amount of a compound having the following formula:

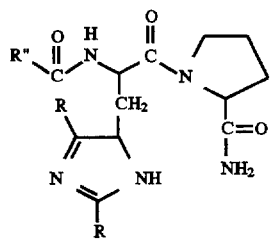

wherein R" is selected from the group consisting of:

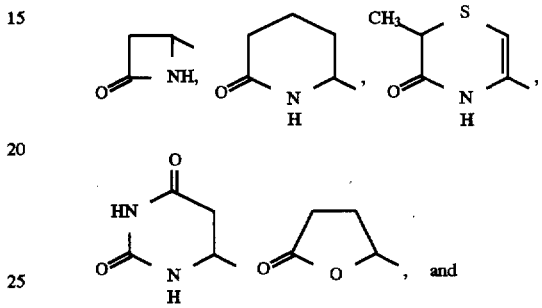

wherein R and R' are respectively:

(a) halogen and halogen;
(b) halogen and hydrogen;
(c) CF$_3$ and hydrogen;
(d) hydrogen and CF$_3$; or
(e) NO$_2$ and hydrogen, wherein said neurologic damage is caused by anesthesia or a drug overdose.

10. The method of claim 7, wherein said animal is a human.

11. The method of claim 7, wherein R and R' are halogen and halogen.

12. The method of claim 11, wherein said halogens are selected from the group consisting of F, I and Br.

13. The method of claim 12, wherein said halogens are both the same.

14. A method for the treatment of effects of neurologic damage in an animal, comprising administering to an animal suffering from neurologic damage a neurologic damage effect treating effective amount of a compound having the following formula:

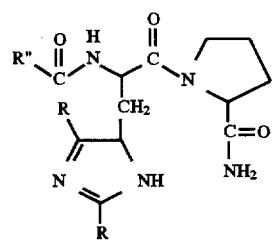

wherein R" is selected from the group consisting of:

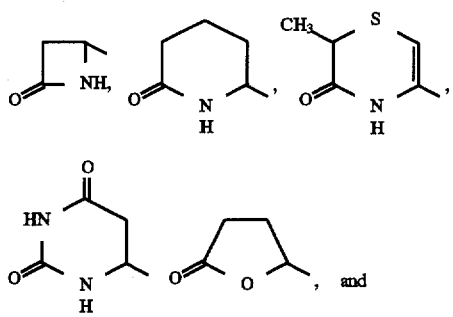

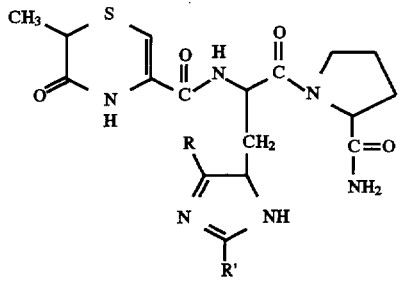

wherein R and R' are respectively:
(a) halogen and halogen;
(b) halogen and hydrogen;
(c) CF$_3$ and hydrogen;
(d) hydrogen and CF$_3$; or
(e) NO$_2$ and hydrogen;
and wherein said neurologic damage is selected from the group consisting of brain trauma and spinal cord trauma.

22. The method of claim 7, wherein R" is

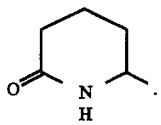

23. The method of claim 7, wherein R" is

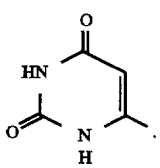

24. The method of claim 7, wherein R" is

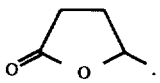

wherein R and R' are are both I and wherein said neurologic damage is selected from the group consisting of brain trauma and spinal cord trauma.

15. The method of claim 7, wherein R and R' are halogen and hydrogen.

16. The method of claim 15, wherein said halogen is selected from the group consisting of F, I and Br.

17. The method of claim 7, wherein R and R' are CF$_3$ and hydrogen.

18. The method of claim 7, wherein R and R' are hydrogen and CF$_3$.

19. The method of claim 7, wherein R and R' are NO$_2$ and hydrogen.

20. The method of claim 7, wherein R" is

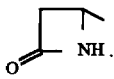

21. A method for the treatment of effects of neurologic damage in an animal, comprising administering to an animal suffering from neurologic damage a neurologic damage effect treating effective amount of a compound having the following formula:

* * * * *